United States Patent
Chang et al.

(10) Patent No.: US 10,450,543 B2
(45) Date of Patent: Oct. 22, 2019

(54) PIPETTE TIP FOR ELECTROPORATION DEVICE

(71) Applicant: LIFE TECHNOLOGIES CORPORATION, Carlsbad, CA (US)

(72) Inventors: Jun-Keun Chang, Seoul (KR);
Keun-Chang Cho, Seoul (KR);
Chan-Il Chung, Gyeonggi-Do (KR);
Neon-Cheol Jung, Gyeonggi-Do (KR);
Seung Gin Huh, Gyeonggi-do (KR)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 411 days.

(21) Appl. No.: 15/357,985

(22) Filed: Nov. 21, 2016

(65) Prior Publication Data

US 2017/0166854 A1    Jun. 15, 2017

Related U.S. Application Data

(62) Division of application No. 13/060,682, filed as application No. PCT/US2009/040698 on Apr. 15, 2009, now Pat. No. 9,523,071.

(30) Foreign Application Priority Data

Apr. 15, 2008 (KR) .................. 10-2008-0034744

(51) Int. Cl.
*B01L 3/00* (2006.01)
*C12M 3/00* (2006.01)
*C12M 1/42* (2006.01)

(52) U.S. Cl.
CPC .................................. *C12M 35/02* (2013.01)

(58) Field of Classification Search
CPC .................. C12M 35/00; C12M 35/02; B01L 2300/0645; B01L 3/502715
See application file for complete search history.

(56) References Cited

U.S. PATENT DOCUMENTS

| 4,099,548 A | 7/1978 | Sturm et al. |
| 5,007,995 A | 4/1991 | Takahashi et al. |

(Continued)

FOREIGN PATENT DOCUMENTS

| EP | 0338667 | 10/1989 |
| JP | S63049070 | 3/1988 |

(Continued)

OTHER PUBLICATIONS

Dong, et al., "Monitoring diclofenac sodium in single human erythrocytes introduced by electroporation using capillary zone electrophoresis with electrochemical detection", Electrophoresis, vol. 22, No. 13, 2001, pp. 2786-2792.

(Continued)

*Primary Examiner* — Nathan A Bowers

(57) ABSTRACT

Provided herein is a pipette tip for electroporation including an outer surface, a void located within the outer surface, and a conductor located at least partially on or within the outer surface, in electrical communication with at least a portion of the outer surface and the void. Further provided herein is a pipette tip for electroporation including a body, a connector, and an elongated part. The connector is located at the distal end of the body and further includes at least one connecting post, a connecting part in mechanical communication with the connector, and a conductor located at least partially on or within the connector, wherein the conductor surrounds at least a portion of the connecting post. The elongated part also has a void and is located at the distal end of the connector. The void of the body, connector, and elongated part are in fluid communication.

15 Claims, 12 Drawing Sheets

(56) References Cited

U.S. PATENT DOCUMENTS

| | | | |
|---|---|---|---|
| 6,001,617 A * | 12/1999 | Raptis | C12M 35/02 435/173.1 |
| 6,074,605 A | 6/2000 | Meserol et al. | |
| 6,241,701 B1 | 6/2001 | Hofmann | |
| 6,287,776 B1 | 9/2001 | Hefti | |
| 6,293,749 B1 | 9/2001 | Raaijmakers et al. | |
| 6,352,853 B1 | 3/2002 | King et al. | |
| 6,356,173 B1 | 3/2002 | Nagata et al. | |
| 6,627,421 B1 | 9/2003 | Unger et al. | |
| 6,628,382 B2 | 9/2003 | Robertson | |
| 6,677,114 B1 | 1/2004 | Schneider et al. | |
| 6,897,069 B1 | 5/2005 | Jarvis et al. | |
| 6,936,462 B1 | 8/2005 | Owen et al. | |
| 7,384,781 B2 | 6/2008 | Moyle et al. | |
| 7,393,681 B2 | 7/2008 | Jarvis et al. | |
| 7,456,012 B2 | 11/2008 | Ryttsén et al. | |
| 7,678,564 B2 | 3/2010 | Muller-Hartmann et al. | |
| 8,017,399 B2 | 9/2011 | Jarvis et al. | |
| 8,101,401 B2 | 1/2012 | Muller-Hartmann et al. | |
| 8,383,394 B2 | 2/2013 | Jarvis et al. | |
| 2002/0090649 A1 * | 7/2002 | Chan | B01J 19/0046 435/7.1 |
| 2003/0009148 A1 | 1/2003 | Hayakawa | |
| 2003/0022153 A1 | 1/2003 | Kirk et al. | |
| 2003/0070923 A1 | 4/2003 | Schroeder et al. | |
| 2005/0164161 A1 | 7/2005 | Augustine et al. | |
| 2007/0275454 A1 | 11/2007 | Chang et al. | |
| 2008/0064511 A1 | 3/2008 | Brace et al. | |
| 2008/0123854 A1 | 5/2008 | Peel et al. | |
| 2010/0196998 A1 | 8/2010 | Jarvis et al. | |
| 2011/0263005 A1 | 10/2011 | Chang et al. | |

FOREIGN PATENT DOCUMENTS

| | | |
|---|---|---|
| JP | H11290058 | 10/1999 |
| JP | 2002504232 | 2/2002 |
| JP | 2007167006 | 7/2007 |
| JP | 2008502356 | 1/2008 |
| KR | 101084528 | 11/2011 |
| WO | 1998058251 | 12/1998 |
| WO | 1999024110 | 5/1999 |
| WO | 2000063408 | 10/2000 |
| WO | 2002033066 | 4/2002 |
| WO | 2003057819 | 7/2003 |
| WO | 2004031353 | 4/2004 |
| WO | 2005123931 | 12/2005 |
| WO | 2006001614 | 1/2006 |
| WO | 2008051169 | 5/2008 |
| WO | 2009129327 | 10/2009 |

OTHER PUBLICATIONS

Hu, et al., "Inhibition of Retroviral Pathogenesis by RNA Interference", Current Biology, vol. 12, Issue 15, 2002, pp. 1301-1311.

Lin, et al., "Electroporation microchips for continuous gene transfection", Sensors and Actuators B, vol. 79, 2001, pp. 137-143.

Nolkrantz, et al., "Electroporation of Single Cells and Tissues with an Electrolyte-filled Capillary", Analytical Chemistry, vol. 73, Issue 18, 2001, pp. 4469-4477.

Osumi, et al., "Gene Transfer into Cultured Mammalian Embyos by Electroporation", Methods, vol. 24, 2001, pp. 35-42.

Speyer, et al., "Multi-Sample Electroporation", BioTechniques, vol. 8, No. 5, 1990, pp. 508.

Speyer, et al., "A Simple and Effective Electroporation Apparatus", Biotechniques, vol. 8, No. 1, 1990, pp. 28-30.

* cited by examiner

[*Prior Art*]

[*Prior Art*]

[*Prior Art*]

[*Prior Art*]

PIPETTE TIP FOR ELECTROPORATION DEVICE

CROSS-REFERENCE

This application is a Division of U.S. application Ser. No. 13/060,682 filed Jul. 13, 2011, now U.S. Pat. No. 9,523,071, and which was a 371 U.S. National Phase Application of PCT/US2009/040698 filed Apr. 15, 2009, which claims priority to and the benefit of Korean Application 10-2008-0034744 filed Apr. 15, 2008, entitled "Pipette Tip for Electroporation Device", which applications are incorporated herein by reference in their entirety.

FIELD OF THE INVENTION

The present invention relates to a pipette tip for electroporation.

BACKGROUND OF THE INVENTION

Electroporation is a technique for introducing macromolecules, which cannot penetrate the cell membrane, into cells using electric pulses. Electroporation is a widely used, and strongly recommended, method for cellular experiments and gene therapy. When a high electric field is applied, the cell membrane becomes temporarily porous and permeable to foreign materials, such as macromolecules. The electropermeabilization of the membrane depends on various parameters of the electric field, such as pulse width, pulse duration, the number of pulses, as well as other experimental conditions. Studies have been performed regarding the above-mentioned parameters in order to understand the mechanism of the electroporation which promotes the effect of transfection. For example, the magnitude of the electric field is reported to be an important parameter for increasing the permeability of the membrane and for controlling the portion of the cell membrane across which transmission occurs.

There are various devices for performing electroporation. FIG. 1 is a perspective view of a prior art cuvette that can be used for performing electroporation. FIG. 2 shows an electroporation device and system described in related U.S. application Ser. No. 10/560,301. FIG. 3 is a side view of the electroporation device shown in FIG. 2. FIG. 4 is a side view illustrating the components of a pipette tip used with the device shown in FIGS. 2 & 3.

An electric field can be applied to a cell suspension and/or gene mixture using the cuvette illustrated in FIG. 1. In such a system, the cuvette may be equipped with two parallel electrode plates 1. When a high electric field is applied between the two electrode plates, the cell membrane becomes permeable, making it is possible to introduce a gene or other foreign matter into the cell. Aluminum electrodes are cheap and may be used with a disposable cuvette. However, using Al creates $Al^{3+}$ ions dissolved from the aluminum electrodes, which ions have been found to negatively influence the cells. Furthermore, when aluminum electrodes are used, the magnitude of the electric field may vary due to a drop in electric voltage caused by the build up of oxide layers on the electrodes. Therefore, to generate a more constant electric field, it may be preferable to use platinum or gold electrodes. However, electrodes made from these materials are costly and therefore it is impractical to use electrodes made from these materials for consumable goods.

Thus, current electroporation devices have the following disadvantages. First, using the cuvette for electroporation may be expensive depending on the electrode material used since there are two electrodes mounted on two opposite side of the cuvette, and since each electrode has a wide surface area. Additionally, it is recommended that the cuvettes be single use. However, many users conduct experiments several times using the same cuvette, thus creating a high possibility of occurrence of experimental error. Second, because the electrode material (Al) is reactive in solution, and the overpotential relative to hydrogen generation is low, performing electroporation using current electroporation devices creates air bubbles due to decomposition of water on the surfaces of the electrodes. Third, the generated ion ($Al^{3+}$) byproduct has been found to have a negative effect on cells. Fourth, surface resistance on the electrode is markedly increased due to the generation of an oxide layer ($Al_2O_3$) on the electrode surface. Fifth, the electric field between electrodes may not remain constant. This may be due to large quantities of current flowing through corners of the electrodes, thereby distorting the electric field. Finally, the sample volume needed may be large, which may make it difficult to analyze a small quantity of cells in the sample. Therefore, there is a need to develop a new electroporation device to address these disadvantages.

FIGS. 2-4 illustrate prior art versions of an electroporation device, pipette tip, and detailed components thereof for solving the above disadvantages. Referring to FIGS. 2-4, current electroporation devices may include a pulse generator 10 for generating an electric pulse; a sample reservoir 20; a pipette 30 with one side in electrical communication with the pulse generator; and a pipette tip 40, one end of which may be inserted onto the end portion of the pipette 30 and the other end of which may be inserted into the sample reservoir 20 and may be in fluid communication with the sample. Additionally, the distal end of the pipette 30, or the pipette tip 40, may be in fluid communication with the sample and the pipette 30 may be capable of drawing a sample into the pipette tip 40. Additionally, an electrode 50 may be inserted into the sample reservoir 20 and may be in fluid communication with the sample. The outer circumferential surface of the pipette 30 comprises a contact body 31 formed with conductive materials, wherein the contact body 31 may be electrically connected with a plunger 42 located inside the pipette tip 40 as shown in FIG. 3. The pipette tip 40 comprises a tubular body 41 which has openings at both ends, wherein the opening at one end may be a ring-shaped section having a relatively large diameter so as to be inserted into the end portion of the pipette 30, and the other end may be a ring-shaped section having a relatively small diameter. The pipette tip 30 is then inserted into the sample reservoir 20, and the plunger 42 located through body 41 of the pipette tip 40.

In performing electroporation using the system and electroporation device shown in FIGS. 2-4, the pipette draws the sample into the interior of the pipette tip 40 while maintaining pressure and thereby keeping the sample within the pipette tip 40. The sample reservoir 20 can then be replaced with a reservoir containing an electrolytic solution. By applying an electric current to the plungers 42 located within the body 41 of the pipette tip 40 and to the electrode 50 contacting the sample in the sample reservoir 40 or the electrolytic solution in the electrolytic solution reservoir, a cell located in the sample drawn into the pipette tip 40 may be electroporated, by passing a current between the two electrodes and through any cells located between the two electrodes. The electroporation of the cells located in the sample within the pipette tip 40 causes the cell membranes to become more permeable, and therefore facilitates the introduction of macromolecules, molecular probes, drugs, DNA, RNA, bacteria, genes, protein material, cells, or any other suitable substance which normally cannot penetrate the cell membrane, into the cell.

In the prior art electroporation system and device as shown in FIGS. 2-4, the outer circumferential surface of the pipette 30 comprises a separate contact body 31, and a separate plunger 42 which may be in electrical communication with the contact body 31 in the body 41 of the pipette tip 40. Since the outer circumferential surface of the pipette 30 includes a separate contact body 31 and a separate plunger 42 in electrical communication connecting with the contact body 31, the structure of the device may be complex which may make manufacturing the device both costly and time consuming. Since the contact body 31 and the plunger 42 formed on the outer circumferential surface of the pipette 30 are connected together in the interior of the device, it may be difficult for a user to determine the state of the connection between the plunger and the contact body.

Therefore, it would be useful to develop an electroporation device where the pipette tip itself can serve as an electrode and thereby apply and electric current to the sample without the need of a separate structure (such as plunger 42) serving as the electrode.

SUMMARY OF THE INVENTION

Provided herein is a pipette tip for use with an electroporation device including an outer surface, a void located within the outer surface, and a conductor located at one side of the outer surface. The conductor is capable of applying an electric field to the void of the pipette tip and thereby applying an electric field to the sample located within the pipette tip and any cells therein. The cell membranes of the cells are then electroporated by the pipette tip, and any material located within the sample can then be transferred into the cells.

Further provided herein is a pipette tip for use with an electroporation device wherein the pipette tip itself serves as an electrode for performing electroporation wherein the pipette tip/electrode contacts the sample without the need of a separate electrode structure. Additionally, the present invention has the added effect of easily performing electroporation by reducing the error rate and reducing the number of trial and error with the simplified design. For example, although meant for single use, cuvettes currently used for electroporation can in fact be used multiple times. With the release of ions into solution from the electrodes located in the cuvettes and the negative effect these ions have on the cells, the error rate between runs can increase. Additionally, because the void of the pipette tip does not contain an additional structure serving as the electrode, such as a plunger which serves as the electrode, the void of the pipette tip of the present invention can easily suction in and expel the sample from the pipette tip by simply using air pressure.

Provided herein is a pipette tip comprising: an outer surface; a void located within the outer surface; and a conductor located at least partially on or within the outer surface, and wherein the conductor is in electrical communication with at least a portion of the outer surface and the void. Having the conductor located at least partially on or within the outer surface of the pipette tip eliminates the need for an electrical conducting structure or an electrode within the void. Thus the void is only filled with the sample. The conductor may be in fluid communication with the void. In some embodiments, the conductor may be ring-shaped. Additionally, the conductor may include a body and a surface, where the body includes a conductive material selected from at least one of copper, brass, nickel, gold, silver, aluminum, any combination thereof, or any other suitable conductive material. In some embodiments, the body of the conductor may be an injection molded conductor, wherein the injection molded conductor includes at least one of plastic or conductive polymer. In some embodiments, the surface of the conductor may include at least one of brass, copper, aluminum, nickel, gold, silver, any combination thereof, or any other suitable conductive material. In some embodiments, the pipette tip may further comprise at least one connecting post. The connecting post may or may not be funnel shaped. In some embodiments, the pipette tip may include at least one, at least two, or at least three connecting posts. In some embodiments, the three connecting posts may be located at 120 degrees in respect to each other and in respect to the outer surface.

Further provided herein is a pipette tip for use with an electroporation device comprising: a body having a proximal end, a distal end, and a void; a connector having a proximal end, a distal end, and a void and further located at the distal end of the body, the connector comprising: at least one connecting post; a connecting part in mechanical communication with the at least one connector; a conductor located at least partially on or within the body and surrounding at least a portion of the at least one connecting post; and an elongated part having a void and located at the distal end of the connector, wherein the void of the body, the connector, and the elongated part are in fluid communication. Having the conductor located at least partially on or within the outer surface of the pipette tip eliminates the need for an electrical conducting structure or an electrode within the void. Thus the void is only filled with the sample. The conductor may or may not be capable of surrounding the at least one connecting post. In some embodiments, the conductor further includes an inner surface capable of applying an electric current to the void of the connector part. In some embodiments, the conductor may be a conductive material selected from at least one of nickel, gold, silver, copper, brass, or aluminum. In some embodiments, the inner surface of the conductor may be plated with a conductive material selected from at least one of brass, aluminum, copper, nickel, gold, silver, any combination thereof, or any other suitable conductive material. In some embodiments, the conductor may be injection molded with plastic or a conductive polymer. Additionally, in some embodiments, the pipette tip may include a combining part diameter and a conductor diameter, wherein the conductor diameter may or may not be less than the combining part diameter. In some embodiments, the elongated part may be tapered along its length. The connecting part may include, in some embodiments, a connecting hole in communication with the void of the combining part. The connecting hole may further include a groove extending radially from the connecting hole. In some embodiments, the connecting part may further include at least one connecting projection and a fixing projection, wherein the at least one connecting projection and the fixing projection are capable of interlocking together.

Provided herein is an electroporation system comprising a pulse generator; a pipette; a pipette tip in electrical communication with the pulse generator, the pipette tip comprising: an outer surface; a void located within the outer surface; a conductor region located at least partially on or within the outer surface, wherein the conductor is in electrical communication with at least a portion of the outer surface and the void; and an electrode in communication with the pulse generator. Having the conductor located at least partially on or within the outer surface of the pipette tip eliminates the need for an electrical conducting structure or an electrode within the void. Thus the void is only filled with the sample. The pipette tip may be in electrical communication with the electrode.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
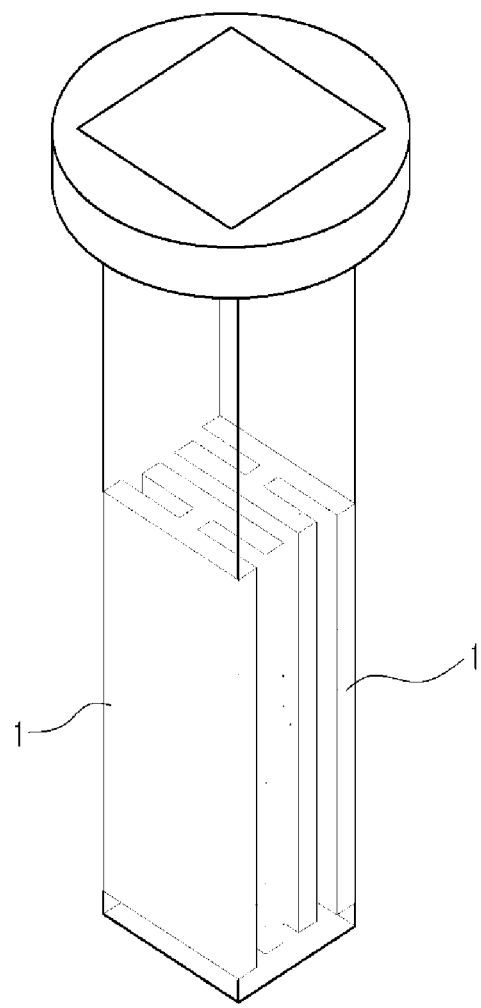
FIG. 1 is a perspective view of a cuvette currently used for performing electroporation.
Figure 2:
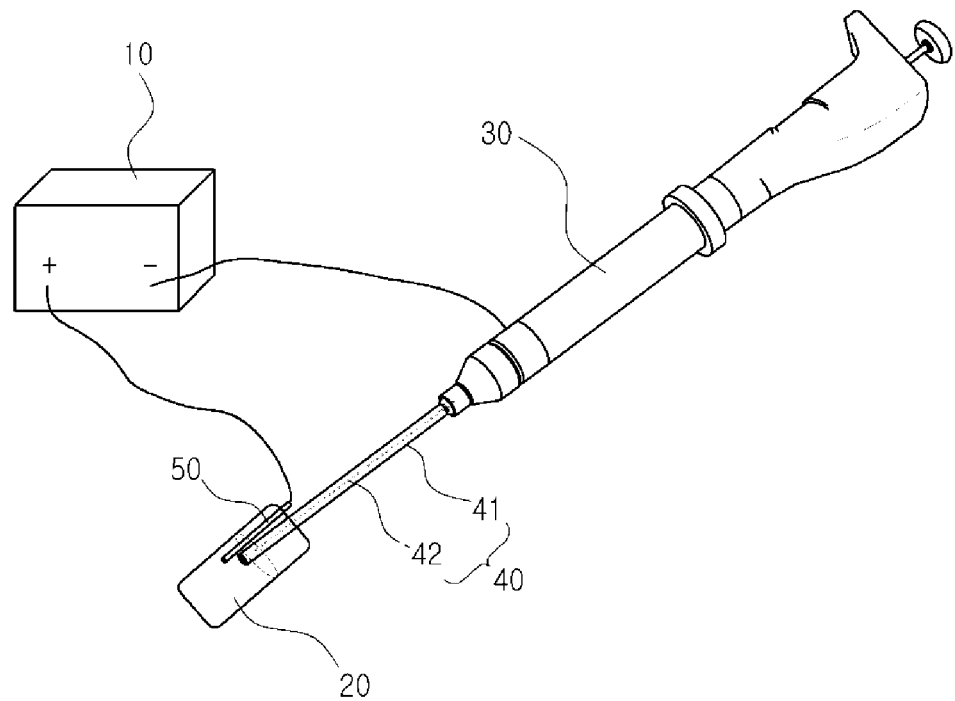
FIG. 2 shows a current embodiment of a system and device used for performing electroporation.
Figure 3:
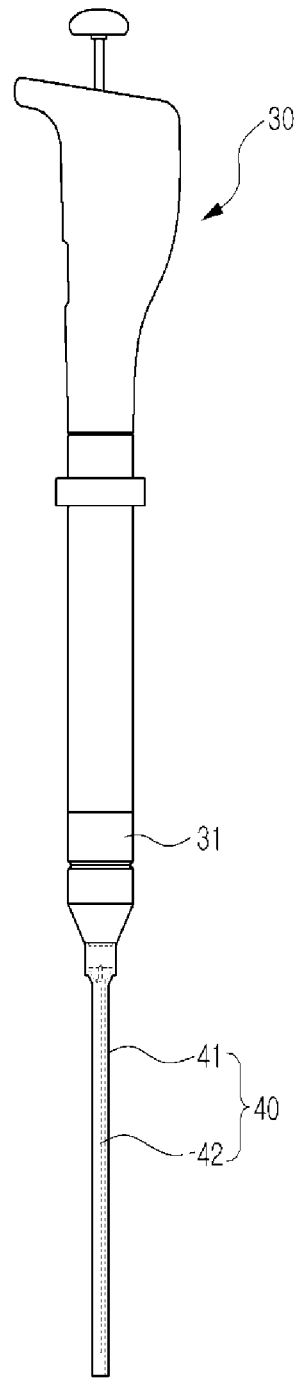
FIG. 3 is a side view of the device shown in FIG. 2.
Figure 4:
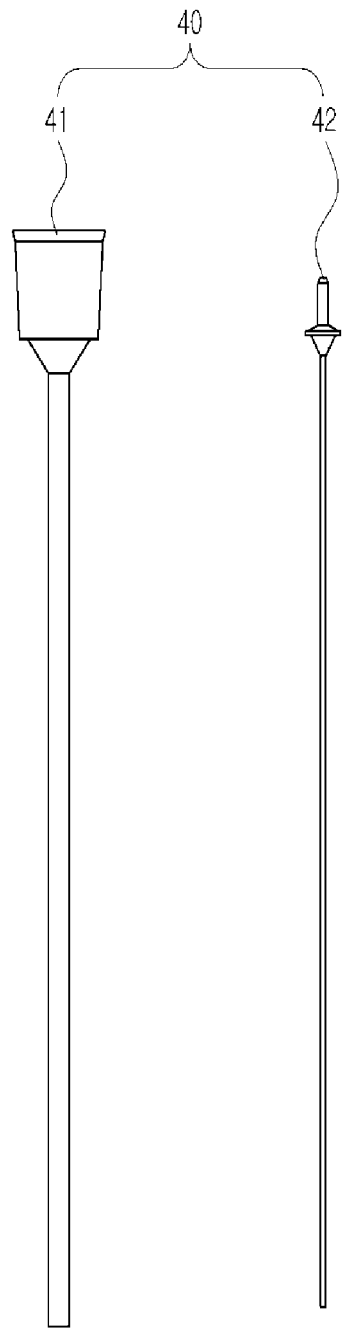
FIG. 4 is a side view of the components of a pipette tip used with the device shown in FIG. 2.

Provided herein is a pipette tip for use with an electroporation device. The pipette tip facilitates electroporation since the pipette tip itself can be used to provide an electrode and/or electric current to the sample without the need of having a separate electrode, such as the plunger electrode shown in FIGS. 3 & 4. Thus, the pipette tip described herein may reduce the unit cost of manufacture of an electroporation device and may thus facilitate performing electroporation on a sample and its contents.

In some embodiments, provided herein is a pipette tip for use with an electroporation device including an outer surface, a void located within the outer surface, and a conductor located at one side of the outer surface. The conductor is capable of applying an electric field to the void of the pipette tip and to any sample and/or cells located within the pipette tip. Application of an electric field to the cell membrane of a cell by the pipette tip electroporates the cells, and material located within the sample may then be transferred into the cells. Examples of material that can be introduced into cells include macromolecules, molecular probes, drugs, therapeutics, DNA, RNA, bacteria, genes, protein material, cells, or any other suitable material.

Figure 5:
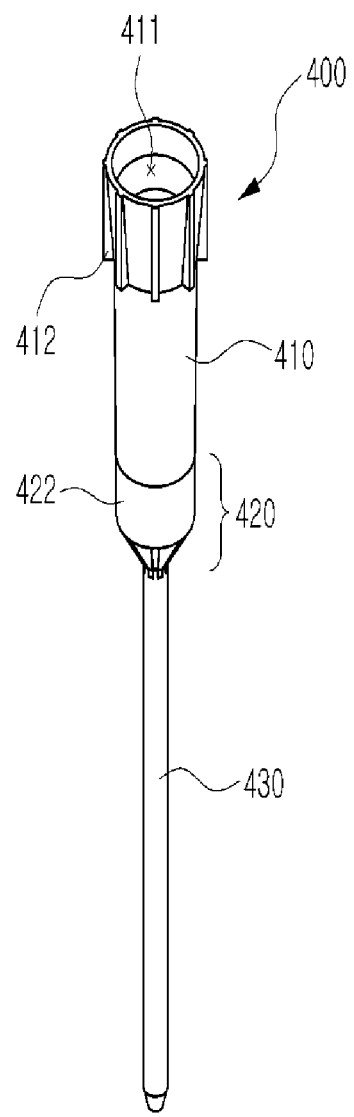
FIG. 5 is a perspective view illustrating an embodiment of the pipette tip.
Figure 6:
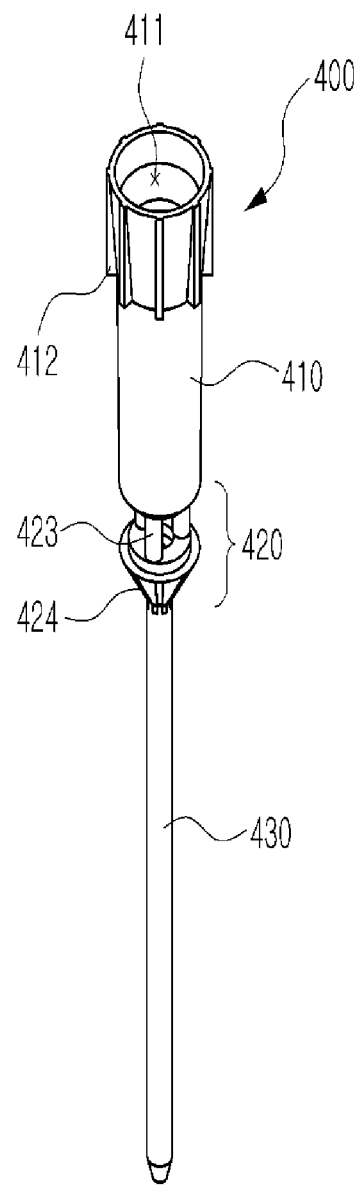
FIG. 6 is a perspective view illustrating the pipette tip shown in FIG. 5 with the conductor removed.
Figure 7:
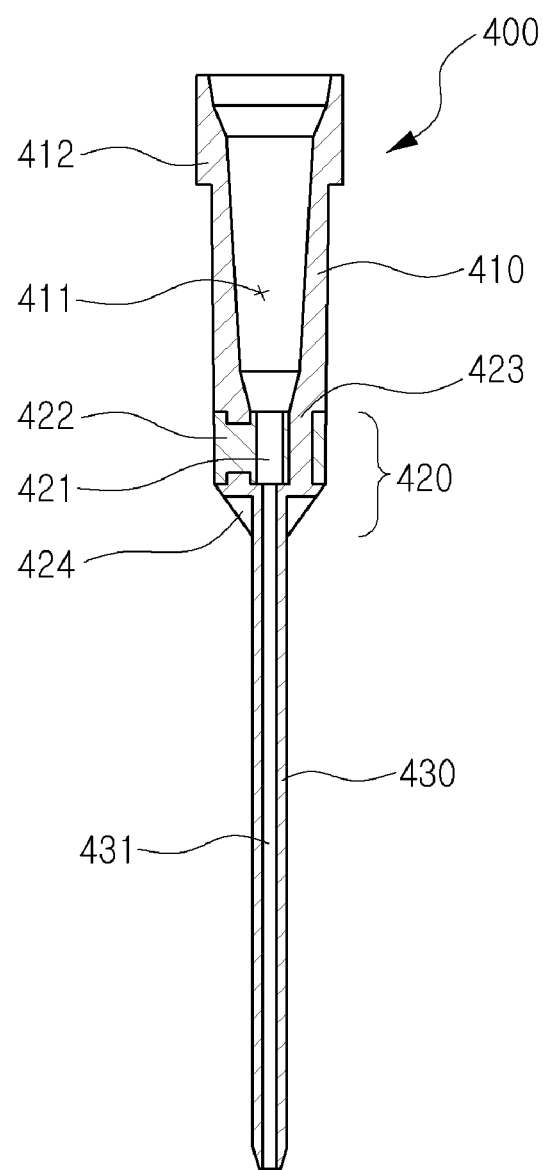
FIG. 7 is a cross sectional view of the pipette tip shown in FIG. 5.
Figure 12:
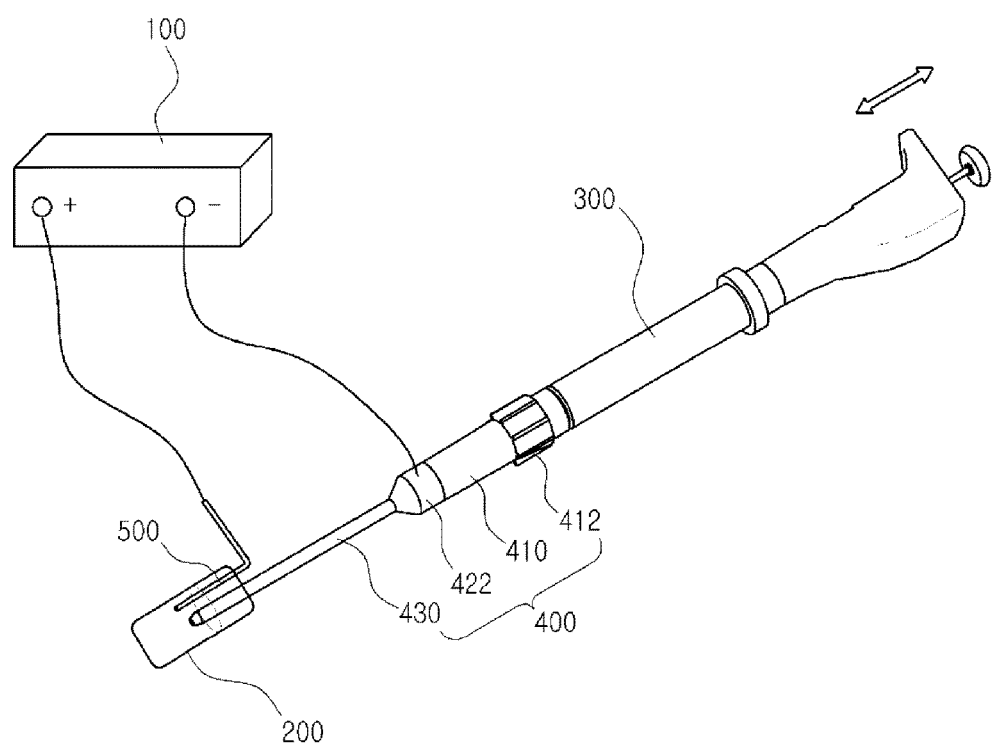
FIG. 12 shows an electroporation device and system.

Referring now to FIGS. 5-7, FIGS. 5-7 show various views of an embodiment of a pipette tip wherein the pipette tip 400 includes: a combining part 410 with a void 411 which may be connected to an end of a pipette 300 (as shown in FIG. 12). The pipette 300 is in fluid communication with the void 411. The pipette tip further includes an elongated part 430 extending from the combining part 410. In some embodiments, the elongated part 430 has a smaller diameter when compared to the combining part 410. A void 431 is also located within the elongated part 430 and is formed so as to contact the sample to be drawn into the pipette tip. The pipette tip further includes a connecting part 420 located between the combining part 410 and the elongated part 430. The connecting part 420 further includes a void 421 which is in communication with the void 411 of the combining part 410 and the void 431 of the elongated part 430. The connection between the voids 411, 421, 431 of the combining part 410, connecting part 420, and elongated part 430, respectively, facilitates the application of an electric field by the connecting part to the sample. In some embodiments, suction can be applied by the pipette 300. When the plunger on the pipette is depressed, suction created by the pipette 300 is transferred through the voids 411, 421, 431 of the combining part 410, connecting part 420, and elongated part 430, respectively, to draw a sample into void 431 of the elongated part 430 and into void 421 the connecting part 420. In some embodiments, the pipette tip 400 is calibrated to draw a sufficient amount of sample, such that the sample only fills the voids 431, 421 of the elongated part 430 and the connecting part 420, respectively. In some embodiments, the sample may be drawn into the voids 411, 421, 431 of the combining part 410, connecting part 420, and elongated part 430, respectively.

The combining part 410 has two ends a distal end, or end furthest from the user/pipette, and a proximal end, or end closest to the user/pipette. Both ends of the combining part 410 have openings, and a void 411 surrounded by an outer surface into which the sample may be drawn. Additionally, an upper outer circumferential surface of the combining part 410 has a predetermined length so as to easily connect or disconnect the pipette tip 400 from the end of the pipette 300, and may further include projections 412 which extend radially from the combining part 410.

Referring to FIG. 6, in some embodiments, the pipette tip includes a connecting part 420 comprising at least one, at least two, at least three, or more than three cylinder-shaped connecting posts 423 fixed on one end of the combining part 410, a funnel-shaped connecting part 424 fixed on the ends of the one or plurality of connecting posts 423; and a conductor 422 surrounding the connecting posts 423. In some embodiments, the conductor is located at least partially on or within the surface of the combining part 410. Having the conductor located at least partially on or within the combining part eliminates the need for an electrical conducting structure, or an electrode, within the void. Thus the void is only filled with the sample. In some embodiments, there may be three connecting posts 423, The conductor 422 may surrounds the connecting posts 423 at least partially or entirely. In some embodiments, the conductor 422 is a ring-shaped conductor. The connecting posts 423 may be disposed at any position around the combining part 420. In some embodiments, the connecting posts 423 may be disposed at an angle of 120° respective to the other connecting posts and relative to the lower surface of the combining part 410, and a void 421 is formed through the center of the connecting part 424. The inner circumferential surface of the conductor 422 may be exposed through gaps between the connecting posts 423 to facilitate the application of electric field to a sample drawn into the pipette tip. In some embodiments, the conductor consists of a conductive material such as, for example purposes only, nickel, gold, silver, copper, brass, aluminum, any combination thereof, or any other suitable conductive material, and/or the surface of the conductor may be plated with a conductive material such as, for example purposes only, nickel, gold, silver, copper, brass, aluminum, any combination thereof, or any other suitable conductive material. In some embodiments, the conductor may be injection molded with a plastic. The surface of the conductor may then be plated with a conductive material such as copper, brass, aluminum, nickel, gold, silver, any combination thereof, or any other suitable conductive material. In some embodiments, the conductor may be injection molded with a conductive polymer.

The elongated part 430 may have any suitable predetermined length in a longitudinal direction of the connecting part 424 by being fixed to the lower surface of the connecting part 424, and a void 431 communicating with the void 421 of the connecting part 424 may be formed through its center. In some embodiments, the elongated part 430 may taper in diameter along its length so as to reduce the quantity of the sample remaining in the end of the elongated part 430 when the pipette tip 400 is removed from the sample reservoir.

Figure 8:
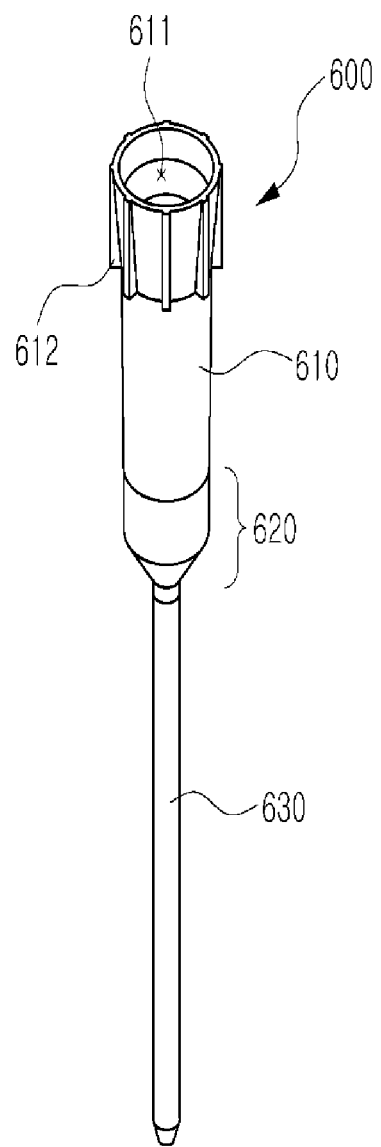
FIG. 8 is a perspective view an embodiment of a pipette tip.
Figure 9:
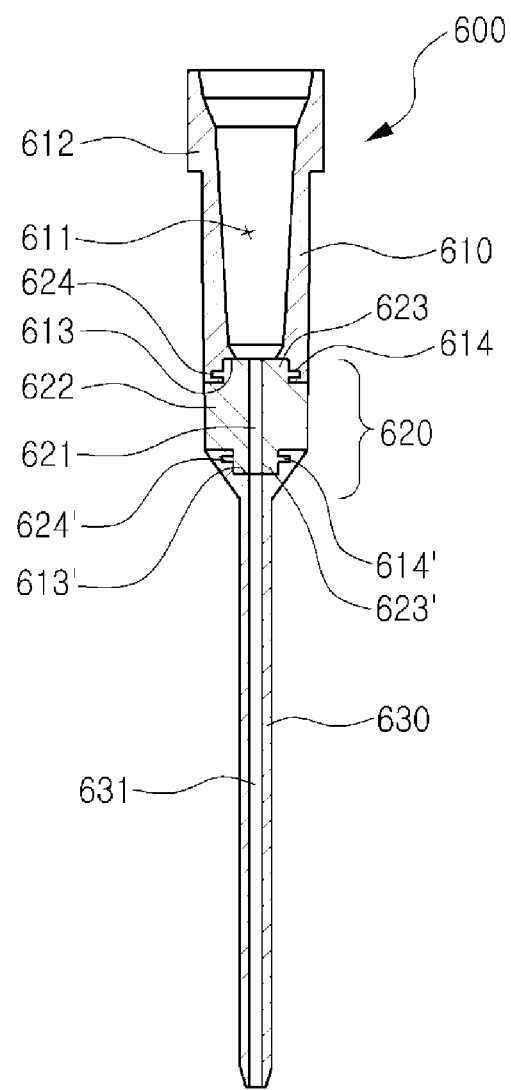
FIG. 9 is a cross sectional view of the pipette tip shown in FIG. 8.

Referring now to FIGS. 8 & 9, FIG. 8 is a perspective view of an embodiment of a pipette tip provided herein, the exterior of which is similar to the pipette tip shown in FIG. 5; FIG. 9 is a cross-sectional view of the pipette tip shown in FIG. 8. The pipette tip 600 for the electroporation device according to another embodiment of the present invention includes: a combining part 610 with a void 611 into which an end of a pipette 300 (as shown in FIG. 12) may be inserted so as to communicate with the void 611; a elongated part 630 having a void 631 into which the sample can be drawn; and a connecting part 620 provided between said combining part 610 and said elongated part 630, having a void 621 inside so that the void 631 of said combining part 630 can communicate with the void 611 of said elongated part 610. The connector part may have a smaller diameter than the combining part 610. The connecting part 620 includes a conductor 622 for applying an electric field to the sample in the void of the pipette tip 600.

The combining part 610 has two ends with openings located at each end and a void 611 in the center. The void 611 is located in the center of the combining part 610. The void 411 is in fluid communication with the voids 421, 431 of the connecting part 420, and the elongated part 430, respectively, into which the sample may be drawn. In some embodiments, the sample may also be drawn into the void 611 of the connecting part 610. The upper outer circumferential surface of the combining part 610 has a predetermined length so as to easily connect or disconnect the pipette tip 600 from the end of the pipette 300, and may further include projections 612 extending radially from the combining part 610.

Referring to FIG. 9, in some embodiments, the pipette tip 600 has a connecting hole 613 communicating with the void 611 formed on a lower surface of the combining part 610, and a ring-shaped groove 614 extending radially from the connecting hole 613 and recessed at the side of the connecting hole 613 so as to fit an upper end of the connecting part 620. A connecting projection 623 having the corresponding shape to the connecting hole 613 of the combining part 610 to be fitted is formed on the upper end, and a fixing projection 624 having the corresponding shape to the connecting groove 614 is formed on the side of the connecting projection 623 to be inserted into the connecting groove 614, thereby connecting the combining part 610 and the connecting part 620. Further, a connecting projection 623' having the corresponding shape to the connecting hole 613' of the elongated part 630 to be fitted thereinto is formed on the lower end, and a fixing projection 624' having the corresponding shape to the connecting groove 614' is formed on the side of the connecting projection 623' to be inserted into the connecting groove 614', thereby connecting the combining part 610 and the elongated part 630.

A void 621 into which a sample may be drawn may be formed through the center of the connecting part 620. The connecting part 620 includes a conductor 622 which may be made from a material selected from a conductive material such as, for example purposes only, nickel, gold, silver, copper, brass, aluminum, any combination thereof, or any other conductive material. The conductor 622 may be located at least partially on or within the surface of the connecting part 620. Having the conductor 622 located at least partially on or within the surface of the connecting part 620 eliminates the need for an electrical conducting structure or an electrode within the void. Thus the void is only filled with the sample. The conductor 622 may thus apply an electric field to the sample located within either the void 621 of the connecting part 620 or the void 631 of the elongated part 630, or both voids 621 and 631. The surface of the conductor may be plated with a conductive material such as, for example purposes only, nickel, gold, silver, copper, brass, aluminum, any combination thereof, or any other suitable conductive material. In some embodiments, the conductor 622 may be injection molded with plastic, the surface of which may then be coated or plated with a conductive material such as, for example, brass, aluminum, copper, nickel, gold, silver, any combination thereof, or any other suitable conductive material. In some embodiments, the conductor 622 may be injection molded with a conductive polymer.

As previously described, the shape of the upper surface of the elongated part 630 may correspond to the shape of the surface of the combining part 610 to facilitate the connection of the combining part 610, the connecting part 620, and the elongated part 630. A void 631 communicating with the combining part 621 of the connecting part 620 is formed through its center and extends in a longitudinal direction. In some embodiments, the elongated part 630 may taper along its length. In some embodiments, the end of the elongated part 630 tapers in diameter from the top or proximal end to the distal end so as to reduce the quantity of the sample in the end of the elongated part 630 when the elongated part 630 is removed from the sample reservoir.

By the above structures, in case of extracting the specimen by using the pipette tip for electroporation according to one embodiment of the present invention, the construction of the electroporation device may be made simpler by making electroporation possible by using the pipette tip itself to apply the electricity to the specimen without having an additional plunger, thereby the present invention can reduce the unit cost of manufacture. Additionally, the present invention can easily perform electroporation by reducing the error rate and reducing the number of trials and errors with a simple structure of applying the electrode to the sample. Also, since current pipette tips for use in an electroporation device may have a separate structure serving as the electrode, such as the plunger described in the prior art, the separate structure may interfere with using air pressure to draw up or eject the sample from the pipette tip. Since the pipette tip for electroporation according to an embodiment of the present invention does not have a separate electrode, the pipette tip may easily draw in or eject a sample using air pressure to create a vacuum or to expulse the sample.

Figure 10:
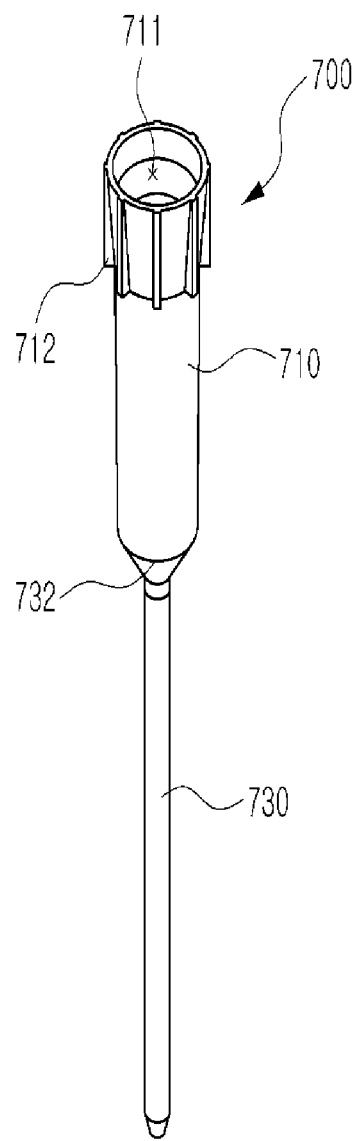
FIG. 10 is a perspective view of an embodiment of a pipette tip.
Figure 11:
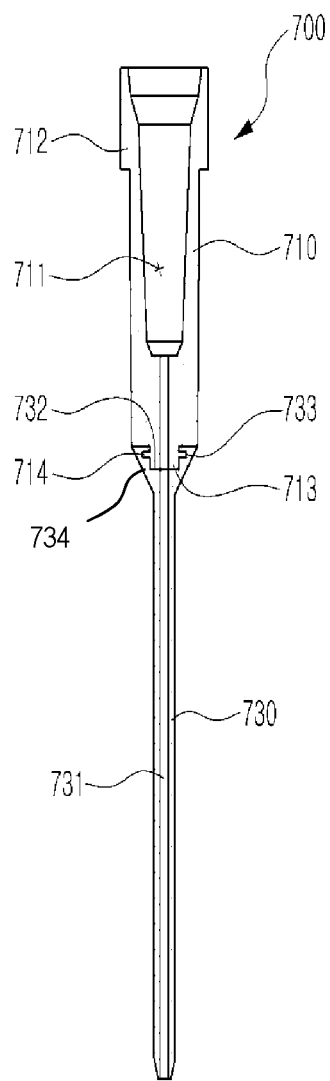
FIG. 11 is a cross sectional view of the pipette tip shown in FIG. 10.

FIG. 10 is a perspective view illustrating an embodiment of a pipette tip provided herein, and FIG. 11 is a cross sectional figure of FIG. 10. Referring now to FIGS. 10-11, the pipette tip 700 for electroporation includes: a combining part 710 with a void 711 into which an end of a pipette 300 is inserted so as to communicate with the void 711; and a elongated part 730 having a void 731 communicating with the void 711 of the combining part 710 into which the sample is drawn into, and a conductor 732 having a relatively smaller diameter than the combining part 710, being fixed to the end of the combining part 710, and consisting of a conductive material on its side. In some embodiments, the conductive material may be on the internal side of the conductor.

The combining part has a proximal end and a distal end, and both proximal and distal ends of the combining part 710 have openings. The combining part also has a void 711 formed through its center into which the sample can be drawn. Additionally, an upper outer circumferential surface of the combining part 710 has a predetermined length so as to easily connect or disconnect the pipette tip 700 from the end of the pipette 300. In some embodiments, the upper outer circumference of the combining part 710 may further include projections 712 formed extending radially from the combining part 710.

A connecting projection 713 having a predetermined height is located on the distal end of the combining part 710. The connecting projection 713 may be inserted into a fixing projection 714 located on the proximal end of the elongated part 730. When joined together, the connecting projection 713 and the fixing projection 714 fix the combining part 710 and the elongated part 730 on the side of the connecting projection 730. A connecting groove 732 having a shape corresponding to the connecting projection 713 may be formed on the proximal end of the elongated part 730 into which the connecting projection 713 to be inserted. In some embodiments, a fixing groove 733, wherein the fixing projection 714 is inserted and combined is formed on inner side of the connecting groove 732. In some embodiments, the end of the elongated part 730 tapers along its length. In some embodiments, the elongated part 730 tapers in diameter from the top or proximal end to the distal end so as to reduce the amount of sample remaining on the end of the elongated part 730 after the elongated part 730 has been removed from the sample reservoir. The conductor 734 may be located at least partially on or within the connecting projection 713. Having the conductor located at least partially on or within the outer surface of the pipette tip eliminates the need for an electrical conducting structure or an electrode within the void. Thus the void is only filled with the sample. In some embodiments, the connector may be located at least partially on or within the combining part 710. In some embodiments, the conductor 734 may consist of conductive materials such as copper, brass, aluminum, nickel, gold, silver, any combination thereof or any other suitable conductive material, and the surface thereof can be plated with any conductive materials such as, for example, copper, brass, aluminum, nickel, gold, silver, any combination thereof, or any other suitable conductive material. In some embodiments, the conductor can be injection molded with plastic, or with a conductive polymer.

Referring now to FIG. 12, FIG. 12 shows an electroporation system including an electroporation device comprising a pipette on which a pipette tip for electroporation may be mounted. Additionally, provided herein is a method of use of the device and system. The electroporation system includes a pulse generator 100 for generating an electric pulse; a sample reservoir 200; a pipette 300 capable of drawing the sample from the sample reservoir and which is capable of maintaining the drawn up sample; a pipette tip 400 electrically connected with the pulse generator 100 of which one end is connected to the end portion of the pipette 300, and of which the other end is inserted into the sample reservoir 200 and into which the sample is drawn into by the pipette 300; and an additional electrode 500 electrically connected with the pulse generator 100 and dipped in the reservoir 200. After the sample is drawn into the pipette tip 400 using the pipette 300 as a pressure maintaining means, a cell or cells, if present, in the sample drawn up into the pipette tip 400 may then be electroporated by applying an electric pulse to the conductors 422 of the electrode 500 and the pipette tip 400 using the pulse generator 100. In some embodiments, the sample reservoir 200 may contain an electrolyte for conducting current, in addition to the sample. In some embodiments, the sample reservoir 200 may be replaced with an electrolyte reservoir containing an electrolyte for conducting current after the sample has been drawn into the pipette tip 400. The pipette tip 400 and the additional electrode 500 may then be placed in the electrolyte reservoir. Pulses of current then can be applied to the cell membrane using the electrode and the pipette tip by passing current between the electrode and the conductor located on the pipette tip. The pulses of current may then change the configuration of the lipid bi-layer of the cell membrane to allow materials located in the sample that are typically unable to pass through the cell membrane to pass through the cell membrane. The pulses applied are of sufficient strength and duration to create temporary pass-throughs for the impermeable materials, which may then reseal without damaging or destroying the cell. Examples of materials that can then be passed through the cell membrane include, but are not limited to, macromolecules, molecular probes, drugs, therapeutics, DNA, RNA, bacteria, genes, protein material, cells, or any other suitable material. The pipette can use vacuum and expulsion to draw in and eject a sample by moving the plunger on the distal end of the pipette as indicated by the arrows in FIG. 12.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for electroporation of a sample, the system comprising:
   a pulse generator;
   a pipette;

a pipette tip configured to be mounted on the pipette, wherein the pipette tip includes a void and a conductor, wherein the void is configured to hold a sample, wherein the conductor is in electrical communication with the pulse generator and is configured to apply an electrical pulse to the sample within the void, wherein the pipette tip includes a plurality of posts, wherein the pipette tip includes a plurality of conductors, and wherein each of the plurality of conductors surrounds at least a portion of each of the plurality of posts.

2. The system of claim 1, wherein the conductor is located at least partially on or within an outer surface of the pipette tip.

3. The system of claim 2, wherein the conductor is ring-shaped.

4. The system of claim 1, wherein the post is funnel shaped.

5. The system of claim 1, wherein the plurality of conductors is disposed in an equiangular set of positions.

6. The system of claim 1, wherein the pipette tip comprises a combining part located at a proximal end of the pipette tip and is configured to mount on the pipette, an elongated part located at a distal end of the pipette tip, and a connecting part located between the combining part and the elongated part.

7. The system of claim 6, wherein the connecting part includes the plurality of posts.

8. The system of claim 7, wherein the plurality of posts is disposed in an equiangular set of positions.

9. The system of claim 8, wherein the plurality of posts comprises three posts, and wherein each post is disposed at an angle of 120° respective to other posts.

10. The system of claim 6, wherein the void comprises a first void within the elongated part, a second void within the connecting part and a third void within the combining part, and wherein the first, second and third voids are in fluid communication.

11. The system of claim 1, wherein the pipette tip does not include an electrode within the void.

12. The system of claim 1, wherein the pipette tip does not include a plunger.

13. The system of claim 1, wherein the pipette and pipette tip are configured to load the sample into the void and remove the sample from the void only using air pressure.

14. The system of claim 1, wherein the conductor comprises a conductive material selected from the group consisting of: nickel, gold, silver, copper, brass and aluminum.

15. The system of claim 1, wherein the conductor comprises a conductive polymer.

* * * * *